United States Patent
Sun (10) Patent No.: US 6,359,199 B1
(45) Date of Patent: *Mar. 19, 2002

(54) ALFALFA PRODUCTS AND METHOD FOR PRODUCING ALFALFA PRODUCTS FOR A SEQUENTIAL HARVESTING SYSTEM

(75) Inventor: Paul L. F. Sun, Roscoe, IL (US)

(73) Assignee: Dairyland Seed Co., Inc, West Bend, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/419,256

(22) Filed: Oct. 15, 1999

Related U.S. Application Data (62) Division of application No. 08/926,169, filed on Sep. 6, 1997, now Pat. No. 6,051,759, which is a division of application No. 08/735,098, filed on Oct. 22, 1996, now Pat. No. 5,724,767, which is a division of application No. 08/362,183, filed on Dec. 22, 1994, now abandoned.

(51) Int. Cl.$^7$ .............................. A01H 5/00; A01H 4/00
(52) U.S. Cl. ...................... 800/320; 800/260; 800/298; 800/266; 800/295
(58) Field of Search ................................ 800/298, 260, 800/266, 295, 320

(56) References Cited

U.S. PATENT DOCUMENTS

| | | | |
|---|---|---|---|
| 3,570,181 A | 3/1971 | Davis | |
| 4,045,912 A | 9/1977 | Sun | ................................ 47/58 |
| 6,051,759 A | * 4/2000 | Sun | ............................ 800/298 |

OTHER PUBLICATIONS

Pamphlet entitled "1995 Alfalfa Guide", AgriPro Seeds Pamphlet, W–L Research, Inc., 2000 Oak Street, Bakersfield, CA 93301.
Pamphlet entitled "The Forage Package", Pioneer® Brand Products for 1994–95, pp. 16–17.
Pamphlet entitled "Pioneer® Brand Products for 1993–94", pp. 14–16.
Hill et al., "Effect of the Number of Parents on Performance of Alfalfa Synthetics", *Crop Science*, vol. 21, Mar.–Apr., pp. 298–300.
Elgin et al. (1983) Use of Strain Crosses in the Development of Multiple Pest Resistance Alfalfa with Improved Field Performance, *Crop Science*, vol. 23, pp 57–64.
Barnes, D.K. et al., "Fall Dormancy in Alfalfa: A Valuable Predictive Tool", Report of the 26th Alfalfa Improvement Conference, South Dakota State University, Brookings, SD Jun. 6–8, 1978, p. 34.
Bellanger et al., "Effects of Harvesting Systems on Yield, Persistence and Nutritive Value of Alfalfa", Abstract from *Canadian Journal of Plant Science* (1992) 72:3, pp. 793–799. 17 ref.
Fehr, Walter R. Principles of cultivar development (1987), pp 417–427.
Poehlman, John Milton. Breeding Field Crops (1987), pp. 652–655.
Song et al. Crop Science (1974)14:pp. 663–666.
Elgin et al. In "Alfalfa and Alfalfa Improvement" (1988) pp. 827–858.
Bula et al. Crop Science (1974) 14: pp 618–621 1974.

* cited by examiner

*Primary Examiner*—Gary Benzion
(74) *Attorney, Agent, or Firm*—Moffa & Sun, P.A.

(57) ABSTRACT

An alfalfa product, hybrids and non-hybrids, and a method for synthesizing an alfalfa product having increased uniformity for preselected traits having improved uniformity of one or more selected traits, including flowering dates, flower frequency, maturity rate, growth rate, fall dormancy and winterhardiness. The alfalfa product may also include improved predictability of these traits. A scheduled harvest system may be established using two or more varieties of the alfalfa product having different and predictable mean flowering dates. The scheduled harvest system may be designed to allow for harvesting of alfalfa varieties at maximum relative feeding value. The method may be used to synthesize an alfalfa product having one or more predetermined traits. The method selects germplasm, including a cytoplasmic male sterile line, a genetic male sterile line, a maintainer line, a restorer line and a line having normal cytoplasm, having agronomically desirable traits. Plants grown from the germplasm are classified and grouped for predetermined traits at different stages of testing and seed increase. The method selects genetically desirable plants having the predetermined traits for seed increase.

18 Claims, 3 Drawing Sheets

ALFALFA PRODUCTS AND METHOD FOR PRODUCING ALFALFA PRODUCTS FOR A SEQUENTIAL HARVESTING SYSTEM

CROSS-REFERENCE TO CO-PENDING APPLICATIONS

This application is a divisional application of copending U.S. application Ser. No. 08/926,169, filed 9/6/97 now U.S. Pat. No. 6,051,759, which is a divisional application of U.S. patent application Ser. No. 08/735,098 filed Oct. 22, 1996, now U.S. Pat. No. 5,724,767, issued 3/10/98, which is a file wrapper continuation of abandoned U.S. patent application Ser. No. 08/362,183, filed 12/22/94 now abandoned.

FIELD OF THE INVENTION

This invention relates to alfalfa, and more particularly to alfalfa products and a method of synthesizing or hybridizing alfalfa products having improved uniformity of selected traits.

BACKGROUND OF THE INVENTION

Plants, and food plants in particular, such as alfalfa play an important role in everyday life. Alfalfa, genus Medicago Sativa, perhaps the most important forage crop species in the world, provides one of the most effective sources of biological nitrogen fixation. While being an extremely energy-efficient food source, alfalfa also provides an excellent source of vitamins and minerals. Alfalfa improves soil tilth making it ideal for crop-rotation. Crop-rotation replenishes nutrients in soil depleted from other crops, such as corn.

The area of alfalfa cut for hay in the United States exceeds 25 million acres. Commercial alfalfa seed may be provided either in a synthetic variety or a hybrid variety. The prior art commercial production of alfalfa seed involves multiple stages. For synthetic varieties the stages may include a breeder seed production stage, a foundation seed production stage, a register seed production stage and a certified seed production stage. Hybrid variety seed production may involve up to three stages including a breeder seed production stage, a foundation seed production stage and a certified seed production stage.

Breeder seed is an initial increase of seed produced from the strains or clones that are developed by a breeder. Foundation seed is a second generation increase of seed produced from the breeder seed. Register seed may be derived from foundation seed. Certified seed may be derived from breeder seed, foundation seed or register seed. Breeder seed descends from a selection of recorded origin, under the direct control of the breeder, a delegated representative or a state or federal inspection service, such as the AOSCA (Association of Official Seed Certification Analysts) in the U.S.A. Certified seed is used in commercial crop production. Certified seed is usually grown, processed and labeled under supervision and-regulation of a public agency.

Efforts in developing healthy and productive alfalfa varieties often focus on breeding for disease and stress-resistant cultivars, for example, breeding for persistence, breeding for adaptation to specific environments, breeding for yield per se, and breeding for quality. Success has been attained in breeding for resistance to such diseases as bacterial wilt, see, e.g., Elgin, Jr., et al., "Breeding for Disease and Nematode Resistance," Alfalfa and Alfalfa Improvement (ed. by Hanson, A. A., et al. 1988), pp. 830–832; anthracnose, id. at 832–833; and common leaf spot, id. at 835–836. Breeders have had less success in breeding for yield and quality per se, although methods have been developed that help increase productivity and yield, see, for example, U.S. Pat. No. 4,045,912 to Sun, incorporated herein by reference. Historically, yield and productivity, quality and persistence are objectives of high concern to farmers.

In the area of breeding for adaptation to specific climates, breeders have developed winterhardy varieties of alfalfa for growing in colder climates. In general, breeders developed winterhardy varieties by using an average fall dormancy score or fall growth score as a predictor. Average fall dormancy scores are made on a scale of one to nine, with a score of nine reflecting the highest fall growth and a score of one reflecting the lowest fall growth. A correlation coefficient as high as 0.95 has been reported between average fall dormancy score and winter injury score. See Barnes, D. K., et al., "Fall Dormancy Score in Alfalfa: A Valuable Predictive Tool," Report of the 26th Alfalfa Improvement Conference, Brookings, S. D. (ed. by Barnes, D. K. Jun. 6–8, 1978), p. 34. However, even in winterhardy varieties of alfalfa, there is significant variation and lack of uniformity among individual alfalfa plants in their degree of winterhardiness; thereby decreasing the potential productivity of these varieties.

A number of other factors also limit the yield and quality of alfalfa fields. In particular, the lack of uniformity in development rate, sometimes measured by flowering dates, is one factor that can cause yield from alfalfa fields to be less than optimal. The highest growth rate for yield and quality of individual alfalfa plants occurs from the early bud to the late bud stage. The date this stage occurs in individual plants varies widely. As a practical matter, however, the harvester of a field of alfalfa must harvest the entire field at one time. As a consequence, when a field of alfalfa plants lacks uniformity in flowering dates or maturity, a high proportion of harvested plants have reduced yield and nutrient value, either because they are too old or too young.

Like flowering dates, another factor that limits the yield of an alfalfa plant may be the lack of uniformity in flowering frequency. Individual alfalfa plants may flower once, twice, three times, ten times or more over the course of a year. Generally, the higher the flowering frequency, the faster the alfalfa plant develops, and the lower the flowering frequency, the slower the alfalfa plant develops. Flower frequency and flowering date vary widely in a population of alfalfa plants. For maximum yield and quality of alfalfa, the producer's harvest frequency should be synchronized with the flowering frequency.

Lack of uniformity in fall dormancy also has reduced the yield and quality of alfalfa fields in both colder and warmer climates. Varieties having uniformity and shorter fall dormancy in either warmer or colder climates may increase the length of the growing season and reduce dormancy time. Consequently, both yield and quality may be increased.

To date, most alfalfa breeding programs emphasize maximizing the heterogeneity of a given alfalfa variety in order to improve yield and stability. This approach, however, results in wide variation in many characteristics, such as flowering dates, flower frequency, development rate, growth rate, fall dormancy and winterhardiness. Prior art breeding methods do not emphasize improving the uniformity of these characteristics. Rather, prior art breeding methods emphasize selection of good germplasm for specific purposes, such as disease resistance, regardless of uniformity for other characteristics.

Prior art methods do not perform selection for desired traits after the stage of increasing seed. Prior art methods also do not include selection of individual plants for the traits of flowering dates, flower frequency, development rate, growth rate and fall dormancy. Furthermore, prior art breeding methods have not included subsequent classification stages of individual plants for these traits.

It is therefore a motivation of the invention to provide alfalfa and an alfalfa product and a process for synthesizing alfalfa and an alfalfa product that improves uniformity of selected traits.

SUMMARY OF THE INVENTION

The invention provides alfalfa and an alfalfa product having improved uniformity of one or more selected traits including flowering dates, flower frequency, development rate, growth rate, fall dormancy and winterhardiness. The alfalfa product may also provide improved predictability of these traits. By using two or more of the invented alfalfa products having different mean flowering dates, a scheduled harvest system may be established. The scheduled harvest system may be designed to allow harvesting of alfalfa varieties at maximum relative feeding value. The invention also includes a method for synthesizing an alfalfa product having increased uniformity for preselected traits.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

To illustrate this invention, a preferred embodiment will be described herein with reference to the accompanying drawings.

DETAILED DESCRIPTION OF PREFERRED EMBODIMENTS

The present invention includes novel varieties of alfalfa that have a high degree of uniformity in one or more selected traits including flowering dates, flower frequency, development rate, growth rate, fall dormancy and winterhardiness. The invention also includes novel varieties of alfalfa that have a high degree of predictability for a selected trait. These novel alfalfa varieties may also have the same level of winterhardiness with the same or specifically different fall dormancy, the same level of winterhardiness with the same or specifically different flower frequencies, the same level of winterhardiness with the same or specifically different flowering dates or specifically different levels of winterhardiness with the same fall dormancy, flower frequencies or flowering dates. These novel alfalfa varieties also may flower significantly earlier than standard (synthetic) varieties for each flowering date or flower significantly later than the standard synthetic varieties for each flowering date. These novel alfalfa varieties produce more consistent, predictable and repeatable results for the characteristics described above than the standard synthetic varieties.

The present invention further includes novel varieties that break their dormancy significantly earlier than the standard varieties, and novel varieties that go to dormancy significantly later than the standard varieties, allowing for an extra cutting or harvest, and thereby extending the productive season for alfalfa.

The present invention includes novel varieties that have a slow development rate and reach maturity for harvest significantly later than the standard varieties, thus reducing harvest frequencies. These novel varieties maintain quality, or relative feeding value (R.F.V.), longer than standard varieties, thus increasing the harvest window for quality. These novel varieties may have the same or faster growth rate, but slower development rate. Furthermore, the invented harvesting system enables alfalfa growers to reduce the risk of a delay in harvesting high quality alfalfa from weather factors such as rain and reduce the risk of rain damage to freshly cut alfalfa.

By using two or more of the present invented novel varieties with different maturities and different flower frequencies, alfalfa growers may select harvest time and harvest frequencies in order to improve labor distribution over harvesting procedures used with standard varieties.

The present invention may include cytoplasmic male sterile (CMS), restorer, maintainer strains and "C" lines, contrasting with the standard (synthetic) strains that use only "C" strains for product development. An "A" line may be defined as a clone or seed line of a cytoplasmic male sterile (CMS) or genetic male sterile plant or seed line. A "B" line may be defined as a clone or seed line of a male sterile maintainer that will produce a CMS when crossed with a CMS. A "C" line may be defined as a clone or seed line with normal cytoplasm that when crossed with a CMS, has progeny that segregates between male fertility and sterility. An "R" line may be defined as a clone or seed line of a male fertility restorer that when crossed with a CMS produces predominately male fertile plants.

A synthesizer of the alfalfa and the alfalfa products may identify the winterhardiness, fall dormancy, flower frequency and flower date-of each individual clone of "CMS", maintainer, restorer and "C" strains. The synthesizer also identifies uniformity of winterhardiness, fall dormancy, flower frequency and flowering dates of the progenies of AxB, AxC, AxR, CxC and the selfing progenies of B, C and R and makes selections for product development.

In one embodiment, the synthesizer planted three hundred seeds from each synthetic population, each clonal progeny and each hybrid population in a greenhouse in January, 1988. The synthesizer transplanted two hundred plants from each population into a field in May 1988.

The clonal progeny and hybrid populations were then studied for variation in winterhardiness, fall dormancy, flowering dates and flowering frequency, and compared against synthetic varieties (Vernal, Magnum plus, WL320 and Saranac). Tables I–IV report the results. Table I sets forth the severity of winter injury recorded for each strain of the synthetic, clonal progeny and hybrid populations. Table II shows a distribution of flower frequency for each population. Table III sets forth the mean flowering date for each flowering date, along with a range, difference and standard deviation. Table IV sets forth fall dormancy distributions for selected populations of the synthetic, clonal progeny and hybrid populations.

TABLE I

Winter Injury of Synthetic Varieties, Clonal Progenies and Experimental Products
Experiment Conducted at D.R.I. Experimental Farm,
Winter of 1988–1989,
Clinton, Wisconsin

| Class | Entry | Pop. Size | No. Injury % | Partial Injury % | Severe Injury % | Winter Kill % |
|---|---|---|---|---|---|---|
| Synthetics | Vernal | 159 | 63.3 | 20.9 | 14.6 | 1.9 |
| | Magnum plus | 163 | 63.8 | 15.3 | 15.3 | 5.5 |
| | WL320 | 157 | 50.3 | 13.4 | 25.5 | 10.8 |
| | Saranac | 150 | 65.3 | 19.3 | 9.3 | 6.0 |

TABLE I-continued

Winter Injury of Synthetic Varieties, Clonal Progenies and Experimental Products
Experiment Conducted at D.R.I. Experimental Farm,
Winter of 1988–1989,
Clinton, Wisconsin

| Class | Entry | Pop. Size | No. Injury % | Partial Injury % | Severe Injury % | Winter Kill % |
|---|---|---|---|---|---|---|
| Clonal Progeny | 5 | 152 | 61.2 | 13.2 | 18.4 | 7.2 |
| | 6 | 105 | 53.3 | 19.0 | 20.0 | 7.6 |
| | 7 | 153 | 49.7 | 15.0 | 26.1 | 9.2 |
| | 8 | 118 | 87.3 | 10.2 | 1.7 | 0.8 |
| | 9 | 118 | 37.3 | 13.6 | 33.1 | 16.1 |
| | 10 | 111 | 17.1 | 18.9 | 42.3 | 21.6 |
| | 11 | 104 | 65.4 | 14.4 | 14.4 | 5.8 |
| | 12 | 164 | 51.2 | 14.6 | 20.1 | 14.0 |
| | 13 | 120 | 55.0 | 16.7 | 20.8 | 7.5 |
| | 14 | 160 | 51.9 | 15.0 | 23.7 | 9.4 |
| | 15 | 109 | 39.4 | 18.3 | 39.4 | 2.8 |
| | 16 | 155 | 80.6 | 4.5 | 8.4 | 6.5 |
| | 17 | 112 | 32.1 | 14.3 | 25.0 | 28.6 |
| | 18 | 112 | 66.1 | 16.1 | 16.1 | 1.8 |
| | 19 | 151 | 73.5 | 13.9 | 9.9 | 2.6 |
| Synthesized Product (Single Cross) | 20 | 152 | 65.8 | 22.4 | 7.9 | 3.9 |
| | 21 | 109 | 78.0 | 12.8 | 6.4 | 2.8 |
| | 22 | 114 | 68.4 | 9.6 | 16.7 | 5.3 |
| | 23 | 110 | 66.4 | 15.5 | 16.4 | 1.8 |
| | 24 | 156 | 53.2 | 15.4 | 19.9 | 11.5 |
| | 25 | 112 | 53.6 | 15.2 | 24.1 | 7.1 |
| | 26 | 93 | 77.4 | 8.6 | 4.3 | 9.7 |
| | 27 | 113 | 75.2 | 14.2 | 8.8 | 1.8 |

TABLE II

Flower Frequencies of Synthetics, Clonal Progenies and Experimental Products

| Class | Entry | Total | (2) | % | (3) | % | (4) | % | (5) | % |
|---|---|---|---|---|---|---|---|---|---|---|
| Synthetic | Vernal | 116 | 6 | 5.2 | 71 | 61.2 | 39 | 33.6 | 0 | |
| | Magnum plus | 104 | 2 | 1.9 | 40 | 38.5 | 62 | 59.6 | 0 | |
| | WL320 | 79 | | | 29 | 36.7 | 48 | 60.8 | 3 | 3.8 |
| | Saranac | 98 | 4 | 4.1 | 55 | 56.1 | 40 | 41.0 | 1 | 1.0 |
| Clonal Progeny | 5 | 76 | | | 41 | 53.9 | 35 | 46.1 | | |
| | 6 | 69 | 13 | 18.8 | 21 | 30.4 | 32 | 46.4 | 3 | 4.4 |
| | 7 | 71 | | | 35 | 49.3 | 36 | 50.7 | | |
| | 8 | 116 | 3 | 2.6 | 80 | 69.0 | 33 | 28.4 | | |
| | 9 | 53 | 8 | 15.1 | 33 | 62.3 | 12 | 22.6 | | |
| | 10 | 19 | | | 2 | 10.5 | 17 | 89.5 | | |
| | 11 | 68 | | | 52 | 76.5 | 16 | 23.5 | | |
| | 12 | 79 | | | 35 | 46.8 | 42 | 53.2 | | |
| | 13 | 66 | | | 6 | 9.1 | 55 | 83.3 | 5 | 7.6 |
| | 14 | 71 | | | 40 | 56.3 | 31 | 43.7 | | |
| | 15 | 43 | | | 39 | 90.7 | 4 | 9.3 | | |
| | 16 | 105 | 4 | 3.8 | 65 | 61.9 | 36 | 34.3 | | |
| | 17 | 36 | | | 14 | 38.9 | 22 | 61.1 | | |
| | 18 | 74 | 1 | 1.3 | 46 | 62.2 | 27 | 36.5 | | |
| | 19 | 85 | | | 83 | 97.6 | 2 | 2.4 | | |
| Synthesized Product (Single Cross) | 20 | 75 | | | 12 | 16.0 | 62 | 82.7 | 1 | 1.3 |
| | 21 | 89 | | | 43 | 48.3 | 46 | 51.7 | | |
| | 22 | 82 | | | 43 | 52.4 | 39 | 47.6 | | |
| | 23 | 87 | | | 34 | 39.1 | 51 | 58.6 | 2 | 2.3 |
| | 24 | 77 | | | 7 | 9.1 | 65 | 84.4 | 5 | 6.5 |
| | 25 | 60 | | | 18 | 30.0 | 42 | 70.0 | | |
| | 26 | 82 | | | 26 | 31.7 | 49 | 59.8 | 7 | 8.5 |
| | 27 | 105 | | | 38 | 36.2 | 67 | 63.8 | | |

TABLE III

Mean, Range and Standard Deviation of 1st, 2nd, 3rd and 4th
Flower Dates of Synthetics,
Clonal Progenies and Experimental Products

| Class | Entry | Init Pop Size | 1st Flower Date | | | | 2nd Flower Date | | | |
|---|---|---|---|---|---|---|---|---|---|---|
| | | | Mean | Range | Diff | S.D. | Mean | Range | Diff | S.D. |
| Synthetics | Vernal | 159 | 157.3 | 143–170 | 27 | 5.19 | 183.9 | 175–192 | 17 | 3.87 |
| | Oneida VR | 160 | 156.2 | 142–168 | 26 | 4.52 | 185.0 | 175–194 | 19 | 3.86 |
| | Magnum plus | 163 | 155.9 | 145–169 | 24 | 4.56 | 182.6 | 172–197 | 15 | 4.32 |
| | Mean | | 156.5 | | 26 | 4.76 | 183.8 | | 17 | 4.02 |
| Clonal Progeny | 10 | 111 | 152.6 | 144–162 | 18 | 4.45 | 188.2 | 182–193 | 11 | 3.47 |
| | 6 | 105 | 154.9 | 143–163 | 20 | 4.42 | 187.8 | 179–196 | 17 | 3.66 |
| | 15 | 109 | 155.1 | 142–163 | 21 | 4.04 | 191.1 | 185–196 | 11 | 2.91 |
| | 13 | 120 | 155.2 | 148–163 | 17 | 3.63 | 183.7 | 179–196 | 11 | 3.98 |
| | 11 | 104 | 155.8 | 143–164 | 21 | 4.74 | 188.9 | 178–195 | 17 | 2.94 |
| | 9 | 118 | 158.1 | 143–166 | 23 | 4.62 | 185.6 | 176–199 | 23 | 5.76 |
| | 19 | 151 | 158.3 | 147–168 | 21 | 3.82 | 185.6 | 175–198 | 23 | 4.46 |
| | 5 | 152 | 158.6 | 148–169 | 21 | 4.82 | 184.7 | 173–194 | 21 | 4.17 |
| | 18 | 112 | 158.6 | 148–166 | 18 | 3.15 | 185.8 | 179–192 | 13 | 2.75 |
| | 14 | 160 | 159.5 | 148–168 | 20 | 4.42 | 183.6 | 175–192 | 17 | 3.46 |
| | 7 | 153 | 159.6 | 145–169 | 24 | 6.30 | 182.8 | 172–191 | 19 | 3.76 |
| | 8 | 118 | 159.9 | 147–169 | 22 | 4.39 | 186.3 | 177–195 | 18 | 3.95 |
| | 16 | 155 | 160.4 | 150–174 | 24 | 4.28 | 183.6 | 172–199 | 27 | 4.42 |
| | Mean | | 157.4 | | 21 | 4.31 | 186.0 | | 18 | 3.82 |
| Synthesized Products Single Cross | 25 | 112 | 156.6 | 147–166 | 19 | 4.19 | 186.8 | 178–194 | 16 | 3.62 |
| | 24 | 156 | 156.7 | 145–167 | 22 | 4.42 | 182.9 | 177–199 | 22 | 4.17 |
| | 20 | 152 | 156.7 | 145–165 | 20 | 4.42 | 182.7 | 173–189 | 16 | 3.79 |
| | 23 | 110 | 157.2 | 144–166 | 22 | 4.58 | 186.6 | 178–199 | 21 | 4.29 |
| | 26 | 93 | 157.2 | 146–165 | 19 | 4.67 | 184.7 | 176–198 | 22 | 4.30 |
| | 27 | 113 | 157.3 | 145–165 | 20 | 4.18 | 186.8 | 176–196 | 20 | 3.53 |
| | 22 | 114 | 157.8 | 144–168 | 24 | 4.63 | 186.5 | 177–194 | 17 | 3.46 |
| | 21 | 109 | 159.8 | 148–172 | 24 | 4.38 | 186.2 | 176–198 | 22 | 3.98 |
| Mean | | | 157.4 | | 21 | 4.43 | 185.4 | | 20 | 3.89 |
| Mean | | | 157.3 | | 21.5 | | 185.7 | | 19.2 | |

| Class | Entry | Init Pop Size | 3rd Flower Date | | | | 4th Flower Date | | | |
|---|---|---|---|---|---|---|---|---|---|---|
| | | | Mean | Range | Diff | S.D. | Mean | Range | Diff | S.D. |
| Synthetics | Vernal | 159 | 218.9 | 207–239 | 32 | 5.79 | 255.7 | 233–269 | 36 | 7.25 |
| | Oneida VR | | 215.8 | 204–244 | 40 | 5.83 | 255.4 | 243–268 | 25 | 6.35 |
| | Magnum plus | 163 | 216.2 | 205–264 | 56 | 7.26 | 254.3 | 238–269 | 31 | 7.72 |
| | Mean | | 217.0 | | 43 | 6.29 | 255.1 | | 31 | 7.11 |
| Clonal Progeny | 10 | 111 | 210.7 | 205–220 | 15 | 4.57 | 249.1 | 240–262 | 22 | 6.90 |
| | 6 | 105 | 214.5 | 205–224 | 19 | 5.05 | 246.6 | 235–263 | 28 | 6.27 |
| | 15 | 109 | 222.9 | 207–250 | 43 | 9.26 | 250.2 | 243–257 | 14 | 4.97 |
| | 13 | 120 | 211.4 | 205–223 | 18 | 4.21 | 249.4 | 240–262 | 22 | 6.74 |
| | 11 | 104 | 220.1 | 209–251 | 42 | 7.24 | 255.7 | 249–265 | 16 | 5.10 |
| | 9 | 118 | 221.3 | 207–257 | 50 | 8.54 | 255.8 | 247–262 | 15 | 4.80 |
| | 19 | 151 | 219.4 | 209–233 | 24 | 6.10 | 257.5 | 248–266 | 18 | 5.25 |
| | 5 | 152 | 217.4 | 206–232 | 26 | 5.74 | 255.6 | 242–265 | 23 | 5.62 |
| | 18 | 112 | 217.4 | 206–234 | 28 | 7.28 | 251.0 | 233–262 | 29 | 7.43 |
| | 14 | 160 | 218.0 | 208–234 | 26 | 5.53 | 255.9 | 243–265 | 22 | 5.95 |
| | 7 | 153 | 214.5 | 205–226 | 21 | 5.01 | 257.0 | 244–267 | 23 | 5.78 |
| | 8 | 118 | 217.0 | 205–243 | 38 | 6.21 | 252.4 | 237–264 | 27 | 7.27 |
| | 16 | 155 | 217.1 | 206–239 | 33 | 6.24 | 256.9 | 241–269 | 28 | 5.97 |
| | Mean | | 217.1 | | 29 | 6.23 | 253.3 | | 22 | 6.00 |
| Synthesized Products Single Cross | 25 | 112 | 212.7 | 205–227 | 22 | 4.13 | 250.2 | 236–267 | 31 | 7.09 |
| | 24 | 156 | 213.0 | 204–235 | 31 | 4.79 | 249.7 | 233–265 | 32 | 6.52 |
| | 20 | 152 | 215.0 | 206–246 | 40 | 6.31 | 252.8 | 238–269 | 31 | 6.11 |
| | 23 | 110 | 213.4 | 205–224 | 19 | 4.49 | 250.9 | 236–264 | 28 | 7.22 |
| | 26 | 93 | 211.7 | 207–235 | 28 | 6.46 | 247.3 | 233–264 | 31 | 7.70 |
| | 27 | 113 | 213.4 | 207–222 | 15 | 3.48 | 251.0 | 237–263 | 26 | 5.34 |
| | 22 | 114 | 216.0 | 207–239 | 32 | 6.65 | 252.9 | 239–266 | 27 | 7.79 |
| | 21 | 109 | 217.1 | 206–244 | 38 | 5.84 | 253.2 | 240–265 | 25 | 6.38 |
| Mean | | | 214.0 | | 28 | 5.27 | 251.0 | | 29 | 6.77 |
| Mean | | | 216.0 | | 21.1 | | 252.8 | | 25.4 | |

| Class | Entry | Init Pop Size | F. Date Total | Range Total | S.D. Total |
|---|---|---|---|---|---|
| Synthetics | Vennal | 159 | 157.8 | 112 | 22.1 |
| | Oneinda VR | | 154.4 | 110 | 20.6 |

TABLE III-continued

Mean, Range and Standard Deviation of 1st, 2nd, 3rd and 4th Flower Dates of Synthetics, Clonal Progenies and Experimental Products

|  |  | Magnum plus | 163 | 151.0 | 126 | 23.9 |
|---|---|---|---|---|---|---|
|  | Mean |  |  | 154.4 | 116 | 22.2 |
| Clonal |  | 10 | 111 | 142.6 | 66 | 19.4 |
| Progeny |  | 6 | 105 | 145.8 | 84 | 19.4 |
|  |  | 15 | 109 | 161.3 | 89 | 21.2 |
|  |  | 13 | 120 | 141.7 | 74 | 18.6 |
|  |  | 11 | 104 | 162.5 | 96 | 20.0 |
|  |  | 9 | 118 | 162.8 | 121 | 23.7 |
|  |  | 19 | 151 | 162.8 | 86 | 19.6 |
|  |  | 5 | 152 | 158.3 | 91 | 20.4 |
|  |  | 18 | 112 | 154.8 | 88 | 20.6 |
|  |  | 14 | 160 | 159.0 | 85 | 19.4 |
|  |  | 7 | 153 | 155.9 | 87 | 19.9 |
|  |  | 8 | 118 | 157.6 | 105 | 21.8 |
|  |  | 16 | 155 | 160.0 | 122 | 20.9 |
|  | Mean |  |  | 155.8 | 92 | 20.4 |
| Synthesized |  | 25 | 112 | 148.3 | 88 | 19.0 |
| Products |  | 24 | 156 | 144.3 | 107 | 19.9 |
| Single Cross |  | 20 | 152 | 149.2 | 107 | 20.6 |
|  |  | 23 | 110 | 150.1 | 90 | 20.6 |
|  |  | 26 | 93 | 142.9 | 100 | 23.1 |
|  |  | 27 | 113 | 150.5 | 81 | 16.5 |
|  |  | 22 | 114 | 155.2 | 100 | 22.5 |
|  |  | 21 | 109 | 158.3 | 109 | 20.6 |
| Mean |  |  |  | 149.9 | 98 | 20.4 |

TABLE IV

Fall Dormancy Distribution of Selected Populations Measurements Were Taken in 1989.

| Class | Entry | Pop. Size | Fall Height in Inches (% of Population) | | | | | | | |
|---|---|---|---|---|---|---|---|---|---|---|
|  |  |  | 1–4 | 5–8 | 9–12 | 13–16 | 17–20 | 21–24 | 25–28 | 29–32 |
| Synthesis | Vernal | 147 | 39.40 | 12.20 | 10.80 | 15.00 | 19.10 | 2.80 | 0.70 |  |
|  | Saranac | 124 | 43.50 | 7.20 | 10.40 | 19.40 | 12.80 | 4.00 | 2.40 |  |
|  | Magnum Plus | 134 | 35.00 | 9.70 | 13.40 | 15.60 | 16.50 | 9.60 |  |  |
| Clonal | 6 | 97 | 20.70 | 12.40 | 2.10 | 20.70 | 29.90 | 10.40 | 4.10 |  |
| Progeny | 7 | 113 | 20.30 | 12.40 | 6.30 | 12.50 | 20.30 | 22.20 | 5.40 | 0.90 |
|  | 8 | 94 | 39.50 | 19.10 | 9.60 | 10.70 | 16.00 | 5.30 |  |  |
|  | 9 | 137 | 55.40 | 11.60 | 8.10 | 11.70 | 9.50 | 3.70 |  |  |
|  | 10 | 128 | 56.30 | 12.40 | 10.10 | 6.20 | 6.30 | 7.10 | 1.60 |  |
|  | 11 | 98 | 32.60 | 10.20 | 9.10 | 28.50 | 14.20 | 4.10 | 1.00 |  |
|  | 12 | 103 | 29.20 | 17.50 | 15.60 | 19.40 | 10.70 | 7.80 |  |  |
|  | 13 | 85 | 44.70 | 7.10 | 20.00 | 19.90 | 5.90 | 1.20 | 1.20 |  |
|  | 14 | 105 | 49.60 | 14.40 | 6.80 | 16.20 | 6.80 | 4.80 | 2.00 |  |
|  | 15 | 144 | 54.20 | 13.30 | 6.30 | 7.70 | 8.40 | 7.70 | 2.80 |  |
|  | 16 | 76 | 54.00 | 18.40 | 10.40 | 5.20 | 7.80 | 3.90 |  |  |
|  | 17 | 141 | 47.60 | 13.40 | 7.00 | 9.20 | 17.10 | 4.90 | 0.70 |  |
|  | 18 | 108 | 16.80 | 13.00 | 13.90 | 20.40 | 18.60 | 12.10 | 4.60 | 0.90 |
|  | 19 | 147 | 23.10 | 12.30 | 18.40 | 27.30 | 12.90 | 4.10 | 2.10 |  |
| Synthesized | 101 | 33 | 18.20 | 48.60 | 30.30 | 3.00 |  |  |  |  |
| Products | 102 | 35 |  | 65.70 | 34.30 |  |  |  |  |  |
|  | 103 | 110 | 2.70 | 45.50 | 42.60 | 9.10 |  |  |  |  |

The results of one study, conducted by the applicant and reported in Tables I–IV, shows that different alfalfa populations and individual plants had different degrees of winterhardiness, different flowering frequencies, different fall dormancy and different flowering dates. Moreover, within populations, there was variation with respect to each of these traits. However, some populations showed less variation and greater uniformity than others with respect to a given trait. For example, Table I shows that in one alfalfa strain of the invention, the population of clonal progeny no. 8 plants, 87.3% of the population exhibited no winter injury, and less than 1% exhibited winter kill. In contrast, in the synthetic variety WL320 population, only 50.3% of the plants exhibited no winter injury, 13.4% exhibited partial winter injury, 25.5% exhibited severe winter injury, and 10.8% exhibited winter kill.

Table II shows the variation in the flower frequencies of each strain. As with winter injury, different populations exhibited different levels of variation in regard to flower frequencies. For example, Saranac shows wide variation in flower frequency, 56.1% of plants flowering three times and 41.0% of plants flowering four times . The population of Clonal progeny no. 8, on the other hand, shows greater uniformity, 69% of plants flowering three times and 28.4% of plants flowering four times. The study, as set forth on Table III, also shows that certain alfalfa populations, for example, the population of clonal progeny No. 13 plants, had a total mean flowering date about 9 days earlier than that of the earliest commercially-available synthetic variety tested (Magnum plus), and some experimental populations, for example, clonal progeny no. 19 plants, had a total mean flowering date about 5 days later than that of the latest commercially-available synthetic variety tested (Vernal).

Finally, Table IV reports the variation in fall dormancy of selected populations. Variation in fall dormancy, as measured by the fall height in inches, varies widely in synthetic strains, such as Saranac, where a large proportion of plants had a measured fall height in inches ranging from 1 to 20 inches. Experimental population 103 shows greatly improved uniformity, having over 88% of plants ranging from 5 to 12 inches.

Product Synthesizing Process

Figure 1A:
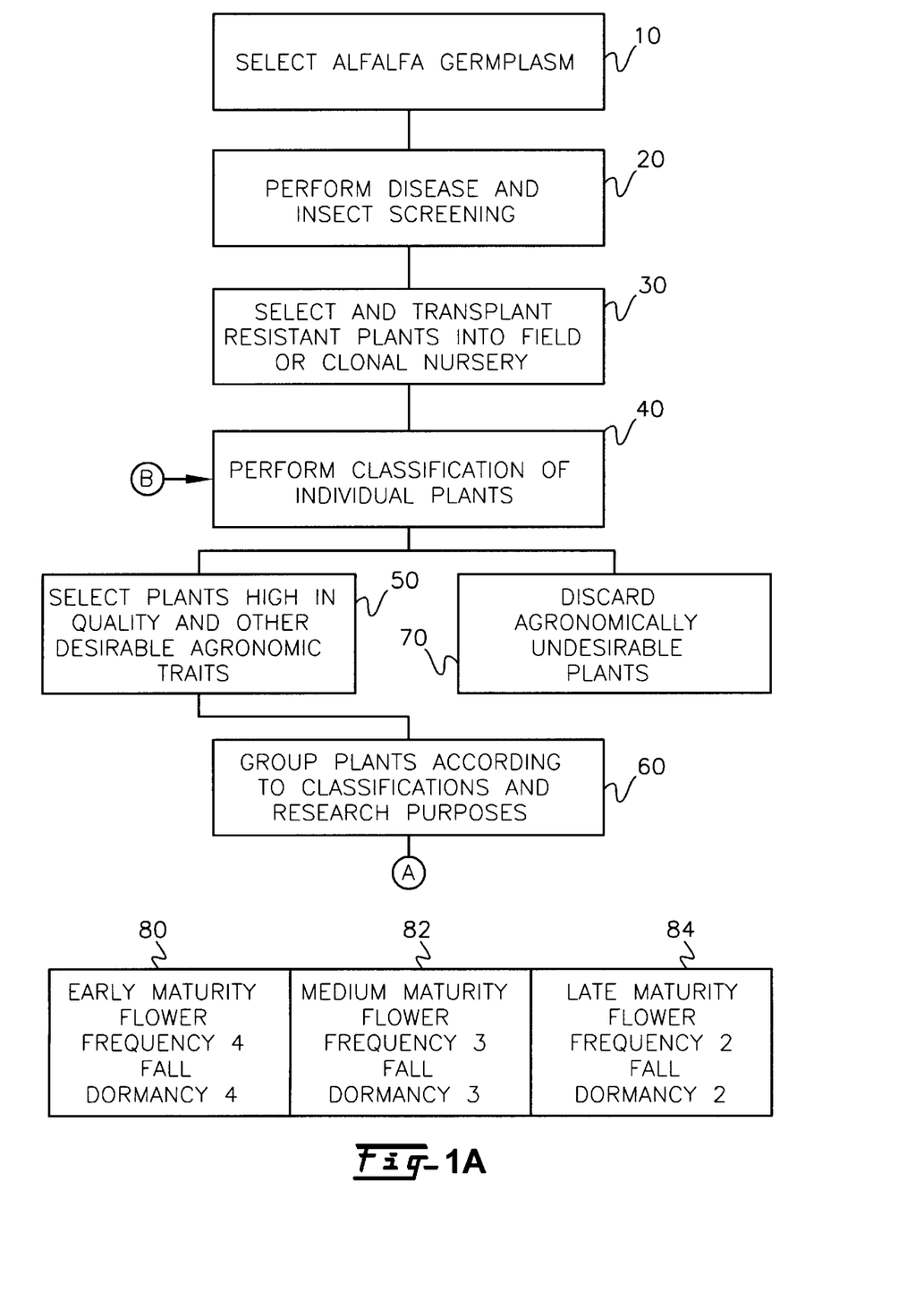
FIGS. 1A and 1B show flow diagrams of one preferred embodiment of a process used to develop novel alfalfa products.
Figure 1B:
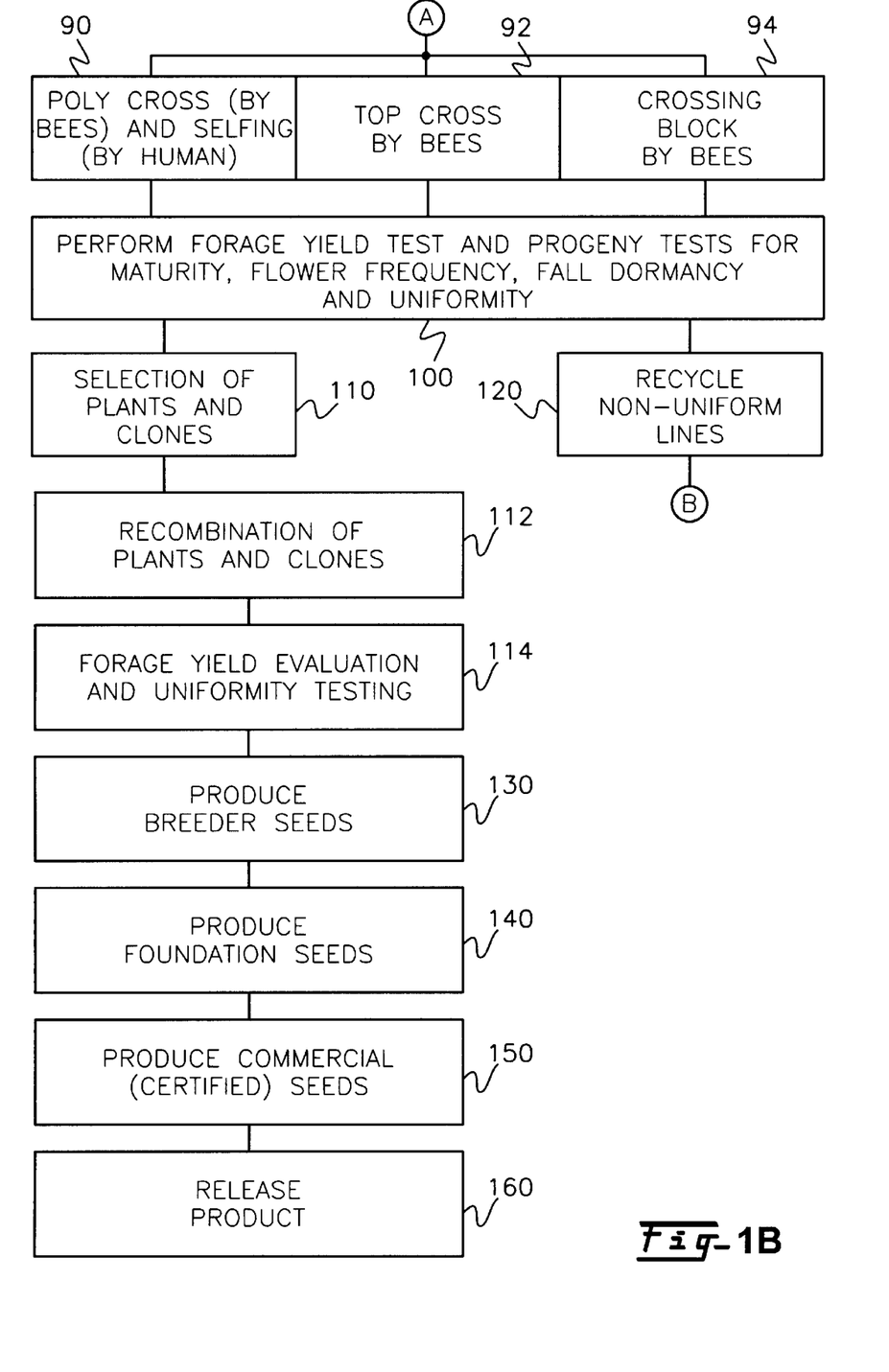

Refer now to FIGS. 1A and 1B which show process flow diagrams of one preferred embodiment of a process used to synthesize the invented alfalfa product. The product synthesis process begins with the selection of suitable alfalfa germplasm in step 10. A synthesizer grows individuals representing each germplasm strain in a greenhouse, a field or both, where each germplasm strain is subjected to disease and insect screening in step 20. In one example embodiment of the method of the invention, the synthesizer plants alfalfa seeds from different alfalfa strains from a germ plasm bank and inoculates them with multiple disease innoculums and insects. The synthesizer selects the healthiest plants in terms of disease resistance and insect resistance in step 30. The synthesizer then transplants the selected plants to a clonal nursery. The synthesizer then inspects each plant individually and classifies each plant into categories in step 40. In one embodiment the synthesizer classifies each plant according to preselected traits such as fall dormancy, winter hardiness, flower frequency and maturity.

After classification, the synthesizer may evaluate each individual plant for quality, or feed value, and other desirable agronomic traits in step 50. The synthesizer groups those plants passing a predetermined threshold according to their classifications and the synthesizer's research and development purposes in step 60. All other plants may be discarded in step 70.

In one example embodiment, the synthesizer groups the plants into three categories 80, 82 and 84. The first category includes plants having the traits of early maturity, four flowerings and a fall dormancy classification of 4. The second category includes plants having the traits of medium maturity, three flowerings and a fall dormancy classification of 3. The third category includes plants having the traits of late maturity, two flowerings and a fall dormancy classification of 2. However, these combinations are given by way of example only, and many other combinations of maturity, flower frequency and fall dormancy are possible and within the scope of the invention.

The synthesizer then ships the plants of each group to a research station where they are planted in a test plot. The groups may undergo a poly cross and selfing, a top cross or a crossing block to produce selfed seeds, poly cross seeds, top cross seeds and single cross hybrid seeds in steps 90, 92 and 94. The synthesizer subjects the seed produced by each group to a forage yield test and a progeny test for uniformity of maturity, uniformity of flower frequency and uniformity of fall dormancy in step 100. In the progeny nursery, the synthesizer records data for each is individual plant. In step 110, the synthesizer selects the plants or clones for which the progeny and $F_1$ seeds have a high degree of uniformity for fall dormancy, flowering frequency and flowering dates and for which the progeny seeds also exhibit high forage yield. The selected plants may include CMS plants, hereinafter referred to as "A" lines, maintainer plants, hereinafter referred to as "B" lines, restorer plants, hereinafter referred to as "R" lines, and male sterility segregating plants, hereinafter referred to as "C" lines. The synthesizer recycles plants failing these tests, such as those from non-uniform lines, in step 120. Recycling may involve selecting plants from selfed seeds and returning them to process step 40.

The synthesizer may produce breeder seeds in step 130 from the selections in step 110. Production of breeder seeds may be done by control pollination using an "A" line (cytoplasmic male sterile strain) with a "B", "C" or "R" line. The synthesizer may also employ random pollination, usually for propagation of a pollenizer line of breeder seeds. Random pollination occurs when a CMS strain is not used. Such crosses, and various advantageous processes for producing alfalfa seeds through the use of such crosses, are described in U.S. Pat. No. 4,045,912 to Sun, entitled "PRODUCTION OF ALFALFA SEEDS". U.S. Pat. No. 4,045,912 is incorporated herein by reference. U.S. Pat. No. 3,570,181 to Davis, entitled "HYBRID ALFALFA PRODUCTION", describes the production and recovery of CMS alfalfa plants. Additionally, at each step of product synthesis, from breeder seed to foundation seed, and from foundation seed to certified seed, the synthesizer may hybridize or synthesize different genetic material for each seed multiplication stage. This practice provides for a reduction of inbreeding.

Alternatively, the synthesizer may recombine the plants and clones in step 112 to produce prebreeder seed. The synthesizer may subject the prebreeder seed to further forage yield evaluation in forage test trials and may space plant the prebreeder seed in progeny nurseries for uniformity tests in step 114. The synthesizer records data for winterhardiness, fall dormancy, flowering frequency, and flowering dates. The synthesizer produces breeder seed from the prebreeder seed showing uniformity in and having predetermined winterhardiness, fall dormancy, flower frequency and flowering dates, and having high forage yields, in step 130.

The synthesizer may produce foundation seeds in step 140 from the breeder seeds. The synthesizer may use control pollination to produce foundation seeds if the breeder seeds produced in step 130 comprise a CMS strain. Otherwise, the synthesizer may produce foundation seeds using random pollination. The foundation seeds may be the source for commercial or certified seeds in step 150. The synthesizer may employ control pollenization to produce 75–100% hybrids for certified seed production. Alternatively, the synthesizer may use a combination of control and random pollination to produce a strain of 75–100% hybrids. In addition, the synthesizer may use the combination of control and random pollination to produce a strain of 74% or less hybrids. The synthesizer releases a product comprising the certified seeds in step 160.

In one example embodiment, the synthesizer may make several types of plantings for breeder seed increase in step 110. First, the synthesizer plants plots of alternating rows of CMS plants from cuttings and maintainer plants from cuttings. The synthesizer may place a "cage" over each plot. The cage prevents contamination from pollen sources other than the maintainer lines. This method allows the CMS plants to produce a hybrid $A_1xB_1$ in a first plot, $A_2xB_2$ in a second plot, etc.

Second, the synthesizer plants plots of alternating rows of CMS plants, from cuttings, and restorer plants, from cuttings or transplants or plants grown from selfed seeds, in isolated areas or in a cage to prevent contamination from pollen sources other than the restorer line. This method allows the CMS plants to produce a hybrid $A_1xR_1$ in a first plot, $A_2xR_2$ in a second plot, etc.

Third, the synthesizer plants plots of alternating rows of CMS plants, from cuttings, and "C" plants, from cuttings or transplants or plants grown from selfed seeds, in isolated fields, or in a cage, to prevent contamination from pollen sources other than a selected "C" line. This method allows the CMS plants to produce a hybrid $A_1xC_1$ in a first plot, $A_2xC_2$ in a second plot, etc.

In each of the above described cases, the synthesizer may use, for example, honey bees, leaf cutter bees, alkali bees, wild bees or other means for pollination. The synthesizer harvests the seed produced from CMS plants in bulk separately from maintainer lines, restorer lines and "C" lines, each of which the synthesizer also harvests separately in bulk. These plantings yield hybrid crosses of AxB, AxR, and AxC.

In one example embodiment, 60% or more plants comprising a strain exhibiting the same fall dormancy score defines the strain to be uniform for fall dormancy. Likewise, 70% or more of the plants comprising a strain exhibiting the same flower frequency defines the strain to be uniform for flower frequency. With respect to flowering dates, 60% or more of the plants comprising a strain having flowering dates within a range of three days defines the strain to be uniform for flowering dates. 70% or more plants comprising a strain exhibiting the same winter injury resistance score defines the strain to be uniform for winter injury resistance.

In one example embodiment, the synthesizer may produce foundation seed in step 140 using the following types of crosses.

AxB Foundation Seed

The synthesizer plants an isolated field in a pattern of separate rows of breeder CMS seed and breeder maintainer seed. The pattern may comprise two or more rows of breeder seed, for example $B_1xB_1xB_1$ or $B_1xB_2$, for every one or more rows of CMS seed. The CMS plants produce hybrid seed, for example $A_1xB_1xB_1$ or $A_1xB_1xB_2$. The synthesizer harvests the seed from the CMS plants in bulk separately from maintainer seed from the maintainer plants.

AxR Foundation Seed

The synthesizer plants an isolated field in a pattern of separate rows of breeder CMS seed and breeder restorer seed. The pattern may comprise two or more rows of breeder seed, for example $R_1xR_1$ or $R_1xR_2$, followed by a vacant row, followed by two or more rows of breeder CMS seed, for example $A_3xB_3$. The CMS plants produce hybrid seed, for example $(A_3xB_3)xR_1$ or $(A_3xB_3)x(R_1xR_2)$. The synthesizer harvests the seed from the CMS plants in bulk separately from restorer seed from the restorer plants.

AxC Foundation Seed

The synthesizer plants an isolated field in a pattern of separate rows of breeder CMS seed and breeder "C" seed. The pattern may comprise two or more rows of breeder seed, for example, $C_1xC_1$ or $C_1xC_2$, followed by a vacant row, followed by two or more rows of breeder CMS seed, for example, $A_1xB_1$. The CMS plants produce hybrid seed, for example $(A_1xB_1)xC_1$ or $(A_2xB_2)xC_2$. The synthesizer harvests seed from the CMS plants in bulk separately from seed from the "C" line plants.

$C_1xC_2$ Foundation Seed

The synthesizer plants an isolated field of breeder seed of two or more "C" lines in rows. The synthesizer harvests the seed in bulk.

In one example embodiment, the synthesizer may produce the certified seed in step 150 as follows.

Hybrid Certified Seed

The synthesizer plants an isolated field of separate rows of CMS and pollenizer seed with the foundation seed. The synthesizer may design these plantings in any fashion to produce at least 75% hybrid seed. In one example, the field design may comprise two to four pollenizer rows, followed by a vacant row, followed with two to eight CMS rows. The pollenizer seed may comprise an AxR, AxC, CxC, inbred, restorer or "C" line. The CMS plants produce a hybrid seed product that may be harvested in bulk separately from the pollenizer line.

Alternatively, the synthesizer may plant a homogeneous mix of CMS and pollenizer seeds in a predetermined ratio. The synthesizer may select the ratio to produce 75% or greater hybrid seed. The synthesizer harvests the hybrid and pollenizer seeds together in bulk. This method may produce a seed product comprising homogeneous assemblage of seeds having a high degree of uniformity for predetermined flowering dates, flower frequency, fall dormancy and winterhardiness.

Non-Hybrid Certified Seed

The synthesizer plants isolated fields with the following possible combinations of foundation seed. The synthesizer may plant only one combination in each isolated field.

AxB and AxR

AxB and AxC

AxB and R

AxB and C

AxB and CxC $A_1xC_1$ and $A_2xC_2$ $C_1xC_2$ and $C_3xC_4$ $C_1$ mixed with $C_2$ The synthesizer harvests the certified seed produced from these plantings in bulk.

The present invention will be described in greater detail by reference to the following examples which are given here for illustrative purposes only and are by no means intended to limit the scope of the present invention.

EXAMPLE 1

Several 10-foot rows, having 30 seeds/row of the commercially-available variety P5432, were planted in 1991 at Clinton, Wis. Data for flowering dates were collected in 1992. Table V sets forth collected flowering date data.

TABLE V

| | P5432 - - Flowering Date | | |
|---|---|---|---|
| | 1st F.D. | 2nd F.D. | 3rd F.D. |
| No. of days for 1st plant to flower | 153 | 174 | 211 |
| No. of days from initial flowering to 60% flowering | 4 | 5 | 6 |

This data shows that for the P5432 seed tested, the first flowering date occurred 153 days from January 1, and within four days, 60% of the plants had flowered. The second flowering date occurred 174 days from January 1, and within five days, 60% of the plants had flowered a second time. The third flowering date occurred 211 days from January 1, and within six days, 60% of the plants had flowered a third time.

EXAMPLE 2

Several 10-foot rows, having 30 seeds/row of seeds from the early maturing experimental cross E93xE92, were planted in 1991 at Clinton, Wis. Experimental cross E93xE92 is derived from a cross between standard Teweles Multistrain CMS and "C" lines. Table VI sets forth flowering date data collected in 1992.

TABLE VI

| | E93 x E92 - - Flowering Date | | | |
|---|---|---|---|---|
| | 1st F.D. | 2nd F.D. | 3rd F.D. | 4th F.D. |
| No. of days for 1st plant to flower | 144 | 170 | 196 | 245 |
| No. of days from initial flowering to 60% flowering | 1 | 3 | 3 | 3 |

This data shows a marked improvement in uniformity of flowering dates. 60% of the $E_{93}xE_{92}$ plants flowered within one day of the first flowering date. The $E_{93}xE_{92}$ plants reached the 60% flowering mark within three days for each of the second, third and fourth flowering dates. Furthermore, for this strain, the $E_{93}xE_{92}$ plants reached the first flowering date a full nine days earlier than the commercial variety P5432.

EXAMPLE 3

Several 10-foot rows, having 30 seeds/row of seeds from the mid-maturity experimental crosses M61xM63 and M3xM11, were planted in 1991 at Clinton, Wis. M61xM63 is a selection from the commercially available Teweles Multistrain blend. Each of these strains was produced by selecting for mid-range maturity, as opposed to early or late maturity. Tables VIIa and VIIb set forth the flowering date data collected in 1992.

TABLE VIIa

| | M61 x M63 - - Flowering Date | | |
|---|---|---|---|
| | 1st F.D. | 2nd F.D. | 3rd F.D. |
| No. of days for 1st plant to flower | 154 | 177 | 202 |
| No. of days from initial flowering to 60% flowering | 0 | 2 | 3 |

TABLE VIIb

| | M3 x M11 - - Flowering Date | | |
|---|---|---|---|
| | 1st F.D. | 2nd F.D. | 3rd F.D. |
| No. of days for 1st plant to flower | 158 | 179 | 202 |
| No. of days from initial flowering to 60% flowering | 0 | 2 | 3 |

This data shows a marked improvement in uniformity of flowering dates as compared against currently available commercial varieties. 60% of the plants flowered on the same day for the first flowering date for M61xM63. 60% of the plants flowered for the second time within two days for the second flowering date and within three days for the third flowering date. 60% of the plants flowered on the same day for the first flowering date for M3xM11, 158 days from January 1. 60% of the plants flowered for the second time within two days for the second flowering date and within three days for the 3rd flowering date.

EXAMPLE 4

Several 10-foot rows, having 30 seeds/row from the late maturing experimental clones L80, experimental cross L45xL47 and experimental cross L21xL22, were planted in 1991 at Clinton, Wis. Self progenies of experimental clone L80 were derived from the product of a cross between a strain produced from a selection from the unknown variety located in Loyal, Wis. and a strain produced from a selection from Durastan. Experimental cross L45xL47 was derived from L45, produced from a Teweles Multistrain x WAPRS x Kanza cross, and L47, a late-maturing selection derived from BIC-5BW. Experimental cross L21xL22 was derived from L21, a late-maturing selection from commercial variety Futura and L22, a late-maturing selection from commercial variety KS204. Tables VIII, IXa and IXb set forth the flowering date data collected in 1992.

TABLE VIII

| | L80 - - Flowering Date | | |
|---|---|---|---|
| | 1st F.D. | 2nd F.D. | 3rd F.D. |
| No. of days for 1st plant to flower | 160 | 191 | 240 |
| No. of days from initial flowering to 60% flowering | 1 | 3 | 1 |

TABLE IXa

| L45 x L47 - - Flowering Date | | | |
|---|---|---|---|
| | 1st F.D. | 2nd F.D. | 3rd F.D. |
| No. of days for 1st plant to flower | 161 | 190 | 229 |
| No. of days from initial flowering to 60% flowering | 1 | 2 | 7 |

TABLE IXb

| L22 x L21 | | | |
|---|---|---|---|
| | 1st F.D. | 2nd F.D. | 3rd F.D. |
| No. of days for 1st plant to flower | 162 | 186 | 229 |
| No. of days from initial flowering to 60% flowering | 0 | 1 | 3 |

This data shows a marked improvement in uniformity of flowering dates. 60% of the L80 and L45xL47 plants flowered within one day for the first flowering date. 60% of the L22xL21 plants flowered on the same day for the first flowering date. For these strains, the 60% flowering mark was reached within 1 to 3 days for the second flowering date. 60% of the L80 plants flowered within 1 day for the third flowering date. The L45xL47 plants showed variation for the third flowering date, reaching the 60% flowering mark within seven days. 60% of the L22xL21 plants flowered within 3 days for the third flowering date. All three strains showed late maturation. For example, the first Julienne flowering dates, 160, 161 and 162 days, respectively, were significantly later than currently available commercial varieties known by the applicant as shown on Table III.

EXAMPLE 5

Several 10-foot rows, having 30 seeds/row from the CMS experimental cross A42xMNB1, were planted in 1991 at Clinton, Wis. The CMS cross A42xMNB1 was derived from the product of a cross between A42, a mid-maturity Vernal selection, and MNB1, a mid-maturity selection from a Minnesota released Phytophthora Resistant germplasm. Table X sets forth the flowering date data collected in 1992.

TABLE X

| A42 x MNB1 - - Flowering Date | | | | |
|---|---|---|---|---|
| | 1st F.D. | 2nd F.D. | 3rd F.D. | 4th F.D. |
| No. of days for 1st plant to flower | 153 | 178 | 203 | 246 |
| No. of days from initial flowering to 60% flowering | 1 | 3 | 3 | 3 |

This data shows a marked improvement in uniformity of flowering dates. Within 1 day of the first flower date, 60% of the A42xMNB1 plants flowered. The A42xMNB1 plants reached the 60% flowering mark within 3 days for each of the second, third, and fourth flowering dates.

EXAMPLE 6

Several 10-foot rows, having 30 seeds/row of seed from the CMS experimental cross A16-691lxMPH2, were planted in 1991 at Clinton, Wis. The CMS cross A16-691xMPH2 was derived from A16-691, a mid-maturity selection from Multistrain X Tempo, and MPH2, a mid maturity selection from Teweles Multistrain. Table XI sets forth the flowering date data collected in 1992.

TABLE XI

| A16-691 x MPH2 - - Flowering Date | | | |
|---|---|---|---|
| | 1st F.D. | 2nd F.D. | 3rd F.D. |
| No. of days for 1st plant to flower | 157 | 182 | 214 |
| No. of days from initial flowering to 60% flowering | 1 | 3 | 3 |

This data also shows a marked improvement in uniformity of flowering dates. 60% of the A16-691xMPH2 plants flowered within 1 day of the first flower date. The A16-691xMPH2 plants reached the 60% flowering mark within 3 days for each of the second and third flowering dates.

Figure 2A:
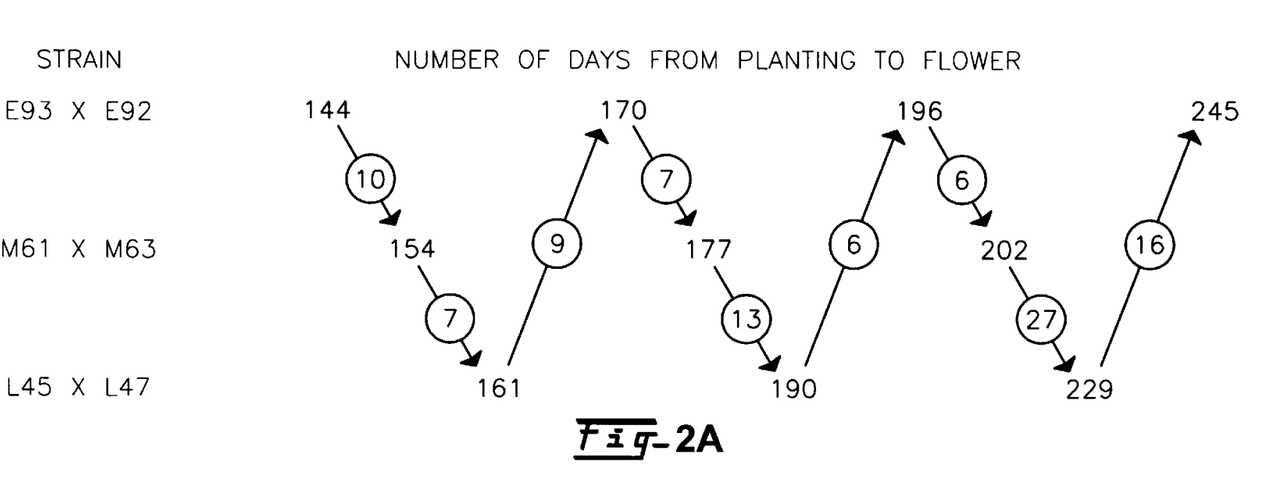
FIGS. 2A and 2B show example embodiments of a harvesting schedule that may be established with the novel alfalfa product of the invention.
Figure 2B:
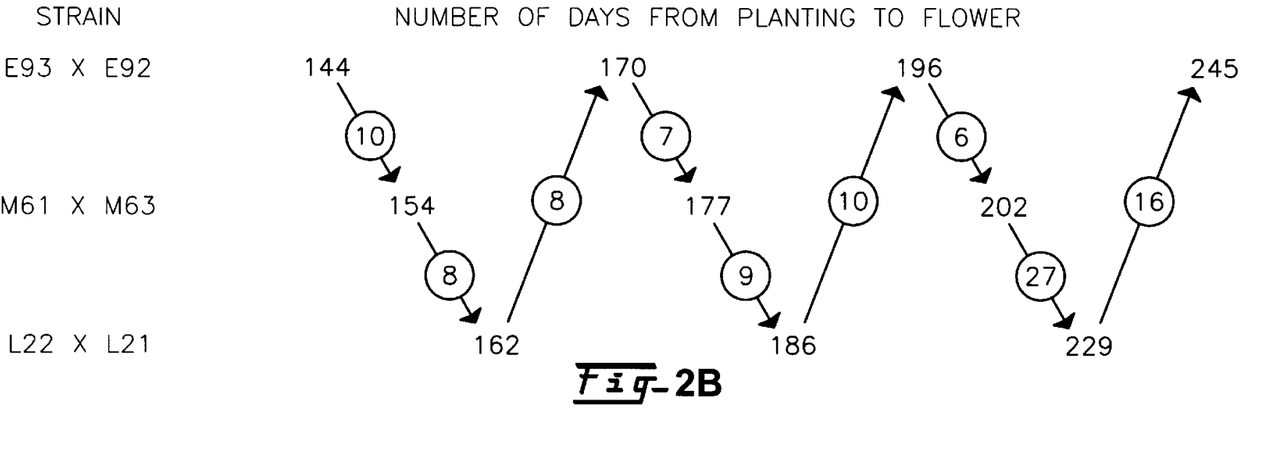

FIGS. 2A and 2B show example embodiments of a harvesting schedule that may be established with the novel alfalfa product of the invention. FIGS. 2A and 2B show the number of days from planting to flowering for three different strains of alfalfa and the number of days between flowerings of the three different strains of alfalfa. A farmer may advantageously use the varieties and strains of the present invention to maximize yield and quality at harvesting. As shown in FIG. 2A, a farmer may plant E93xE92, M61xM63 and L45xL47 strains in separate 40-acre fields. The farmer may then harvest the fields according to the flowering date schedule shown in FIG. 2A. The farmer may harvest the field having alfalfa at a desired maturity to provide for a maximum quality of the alfalfa. In contrast, if a farmer were to plant a 100 acre field with, for example, only standard Vernal or Saranac varieties, or both, the farmer would have to harvest the entire field at the same time to maximize the quality of the alfalfa. As one harvester generally may cut only about 40 acres per day, and as a progressive dairy farmer generally grows more than a hundred acres of alfalfa for feed, ordinary commercial is varieties result in inefficient harvesting in terms of maximizing quality of the product. Similarly, the farmer may schedule harvesting according to FIG. 2B, using the E93xE92, M61xM63 and L22xL21 strains. The harvesting schedule provides the following advantages.

1. Maximizes alfalfa product quality at harvest.
2. Reduces the magnitude of risk of weather (rain) damage to alfalfa in the drying process after cutting.
3. Reduces the magnitude of risk of weather (rain) damaging the quality of alfalfa by delaying harvest.
4. Increases labor distribution efficiency.
5. Use of early maturity alfalfa provides feed earlier.
6. Use of late maturity alfalfa will provide a wider harvest window.
7. Selecting a proper maturity alfalfa for a given geographic area may reduce the risk of winter kill.

Those modifications and equivalents which fall within the spirit of the invention are to be considered a part thereof.

The invention has been described herein in considerable detail in order to comply with the Patent Statutes and to provide those skilled in the art with the information needed is to apply the novel principles and to construct and use such specialized components as are required. However, it is to be understood that the invention can be carried out by specifically different methods and technologies, and that various modifications, both as to the technological details and operating procedures, can be accomplished without departing from the scope of the invention itself.

What is claimed is:

1. An alfalfa product having a significant improvement of a uniformity of flowering date trait comprising a plurality of alfalfa plants, wherein each alfalfa plant has a plurality of flowering dates, wherein the alfalfa product has a mean flowering date for each of the plurality of flowering dates and a standard deviation measuring an absolute difference of each of the plurality of flowering dates, for each alfalfa plant from a respective mean flowering date, computed from the plurality of flowering dates and wherein the alfalfa product has a standard deviation at least seven-and-one-half percent (7.5%) less than a second standard deviation, for at least two flowering dates of the plurality of flowering dates, of an alfalfa variety selected from the group consisting of Vernal, Oneida VR and Magnum plus, under substantially similar environmental conditions.

2. The alfalfa product of claim 1 wherein a mean first flowering date of the plurality of flowering dates is at least five days earlier than a mean first flowering date for an alfalfa variety selected from the group consisting of Vernal, Oneida VR and Magnum plus, under substantially similar environmental conditions.

3. The alfalfa product of claim 1 wherein a mean first flowering date of the plurality of flowering dates is at least five days later than a mean first flowering date for an alfalfa variety selected from the group consisting of Vernal, Oneida VR and Magnum plus, under substantially similar environmental conditions.

4. The alfalfa product of claim 1 wherein each of the plurality of alfalfa plants have a flower frequency and at least seventy percent of the flower frequencies of the plurality of alfalfa plants are equal to a preselected flower frequency.

5. The alfalfa product of claim 1 wherein the alfalfa product is synthesized from progenies of a two clones cross.

6. The alfalfa product of claim 1 wherein the alfalfa product is synthesized from a cytoplasmic male sterile line with a pollenizer line cross.

7. The alfalfa product of claim 1 wherein the alfalfa product is synthesized from a single cross.

8. The alfalfa product of claim 1 wherein the alfalfa product is synthesized from progeny of a single clone.

9. The alfalfa product of claim 1 wherein the standard deviation of the alfalfa product is at least seven-and-one-half percent (7.5%) less than the second standard deviation, for each respective mean flowering date of the plurality of mean flowering dates, of an alfalfa variety selected from the group consisting of Vernal, Oneida VR and Magnum plus, under substantially similar environmental conditions.

10. An alfalfa product having a significant improvement of a uniformity of flowering date trait comprising a plurality of alfalfa plants, wherein each alfalfa plant has a plurality of flowering dates, wherein the alfalfa product has a mean flowering date for each of the plurality of flowering dates and a standard deviation measuring an absolute difference of each of the plurality of flowering dates, for each alfalfa plant from a respective mean flowering date, computed from the plurality of flowering dates, wherein the alfalfa product further has a summed standard deviation equal to a sum of the standard deviations of the first four flowering dates of the plurality of flowering dates, and wherein the alfalfa product has a summed standard deviation at least fifteen percent (15%) less than a second summed standard deviation of an alfalfa variety selected from the group consisting of Vernal, Oneida VR and Magnum plus, under substantially similar environmental conditions.

11. The alfalfa product of claim 10 wherein a mean first flowering date of the plurality of flowering dates is at least five days earlier than a mean first flowering date for an alfalfa variety selected from the group consisting of Vernal, Oneida VR and Magnum plus, under substantially similar environmental conditions.

12. The alfalfa product of claim 10 wherein a mean first flowering date of the plurality of flowering dates is at least five days later than a mean first flowering date for an alfalfa variety selected from the group consisting of Vernal, Oneida VR and Magnum plus, under substantially similar environmental conditions.

13. The alfalfa product of claim 10 wherein each of the plurality of alfalfa plants have a flower frequency and at least seventy percent of the flower frequencies of the plurality of alfalfa plants are equal to a preselected flower frequency.

14. An alfalfa product having a significant improvement of uniformity of a flowering frequency trait comprising a plurality of alfalfa plants wherein the alfalfa product has a preselected flower frequency and wherein a first percentage of the plurality of alfalfa plants having the preselected flower frequency is at least fifteen percent (15%) higher than a second percentage of alfalfa plants having the same flower frequency of any flower frequency of an alfalfa variety selected from the group consisting of Vernal, Magnum plus, WL320 and Saranac, under substantially similar environmental conditions.

15. An alfalfa product suitable for use in a sequential harvesting system, wherein the alfalfa product further comprises a plurality of varieties each having at least one flowering date, wherein each variety of the plurality of varieties has a mean flowering date for each flowering date of the at least one flowering date, and each mean flowering date of each variety of the plurality of varieties is separated by at least three days from each other mean flowering date of each variety of the plurality of varieties.

16. The alfalfa product of claim 15 wherein the alfalfa product has an improved uniformity of a flowering date trait and an improved uniformity of a flower frequency trait.

17. The alfalfa product of claim 15 wherein the alfalfa product has a reduced development rate wherein the alfalfa product further maintains quality for a longer period.

18. An alfalfa product having a significant improvement of a uniformity of flowering date trait comprising a plurality of alfalfa plants, wherein each alfalfa plant has a plurality of flowering dates, wherein the alfalfa product has a plurality of product measures, wherein each product measure is equal to a number of days from an initial flowering day to a day where at least sixty percent (60%) of the plurality of alfalfa plants have flowered, for each respective flowering date of the plurality of flowering dates, wherein a commercial variety P5432 has a plurality of control alfalfa plants having a plurality of control flowering dates, and further has a plurality of control measures of a number of days from a control initial flowering day to a control day where at least sixty percent (60%) of the plurality of control alfalfa plants have flowered, for each respective control flowering date of the plurality of control flowering dates, and wherein the product measure for each flowering date of the plurality of flowering dates is at least two days less than a respective control measure for each control flowering date of the plurality of control flowering dates.

* * * * *

UNITED STATES PATENT AND TRADEMARK OFFICE
CERTIFICATE OF CORRECTION

PATENT NO.    : 6,359,199 B1
DATED         : March 19, 2002
INVENTOR(S)   : Sun

It is certified that error appears in the above-identified patent and that said Letters Patent is hereby corrected as shown below:

<u>Column 1,</u>
Line 9, after the words "Pat. No. 6,051,759," insert the words -- issued 4/18/00, --.
Line 56, delete the "-".

<u>Column 2,</u>
Line 48, delete the word "date" and replace it with -- dates --.

<u>Column 4,</u>
Line 58, delete the "-".

<u>Column 7,</u>
Table III, line 5, delete the words "17" and the "4.02" and replace it with -- 17 -- in the "Diff" column and -- 4.02 -- in the "S.D." column.

<u>Column 10,</u>
Line 66, delete the extra space after the word "times".

<u>Column 11,</u>
Line 67, delete the word "is".

<u>Column 12,</u>
Line 49, delete the word "pollenization" and replace it with the word -- pollination --.

<u>Column 14,</u>
Line 19, after the word "comprising" insert the word -- a --.

UNITED STATES PATENT AND TRADEMARK OFFICE
CERTIFICATE OF CORRECTION

PATENT NO. : 6,359,199 B1
DATED : March 19, 2002
INVENTOR(S) : Sun

It is certified that error appears in the above-identified patent and that said Letters Patent is hereby corrected as shown below:

Column 19,
Line 23, delete the word "is".

Signed and Sealed this

Eighth Day of October, 2002

Attest:

Attesting Officer

JAMES E. ROGAN
*Director of the United States Patent and Trademark Office*